United States Patent

Shaffer et al.

[11] Patent Number: 6,105,572
[45] Date of Patent: Aug. 22, 2000

[54] LIQUID VENTILATOR

[75] Inventors: Thomas H. Shaffer, Landowne; Marla R. Wolfson, Philadelphia; James L. Heckman, Ambler, all of Pa.; John Hoffman, Poway, Calif.

[73] Assignees: Alliance Pharmaceutical Corp., San Diego, Calif.; Temple University of the Commonwealth System of Higher Education, Philadelphia, Pa.

[21] Appl. No.: 08/966,340

[22] Filed: Nov. 7, 1997

[51] Int. Cl.[7] ................................................ A61M 16/00
[52] U.S. Cl. ................ 128/200.24; 128/913; 128/207.14
[58] Field of Search ............................ 128/200.24, 913, 128/207.14

[56] References Cited

U.S. PATENT DOCUMENTS

| | | | |
|---|---|---|---|
| 4,232,665 | 11/1980 | Vaseen | 128/200.24 |
| 5,335,650 | 8/1994 | Shaffer et al. | 128/200.24 |
| 5,437,272 | 8/1995 | Fuhrman | 128/203.12 |
| 5,492,109 | 2/1996 | Hirschl et al. | 128/207.14 |
| 5,706,830 | 1/1998 | Parker | 128/207.14 |
| 5,707,352 | 1/1998 | Sekins et al. | 604/56 |

FOREIGN PATENT DOCUMENTS

WO 93/09833  5/1993  WIPO .
WO 97/19719  6/1997  WIPO .

*Primary Examiner*—John G. Weiss
*Assistant Examiner*—Virendra Srivastava
*Attorney, Agent, or Firm*—Knobbe, Martens, Olson & Bear LLP

[57] ABSTRACT

A liquid ventilator having a dual loop, single pump configuration is disclosed. The liquid ventilator preferably utilizes two three-way valves for routing liquid from a reservoir in a regeneration apparatus and to a patient's pulmonary system, and back to the reservoir again. A controller controls the configuration of the three-way valves and the pump speed of the motor to allow user control over the parameters of inspiration and expiration.

25 Claims, 7 Drawing Sheets

LIQUID VENTILATOR

BACKGROUND OF THE INVENTION

The present invention relates to apparatus for performing total liquid ventilation on patients. More particularly, the invention is related to inspiration and expiration pumping systems for liquid ventilators.

Liquid ventilation is a procedure involving temporarily filling pulmonary air passages with an oxygenated liquid medium. It was first demonstrated that mammals submerged in hyperoxygenated saline could breathe liquid and successfully resume gas breathing in 1962. However, this approach to liquid ventilation (LV) was eventually abandoned, due to the practical difficulties of dissolving sufficient quantities of $O_2$ in saline (even at hyperbaric pressures), and because saline rinses away much of the surfactant lining the lung alveoli. These problems were overcome in 1966 by Dr. Leland Clark, who was the first to use perfluorocarbon liquids (now oxygenated at atmospheric pressure) to support the respiration of mice, cats, and puppies.

Perfluorocarbon (PFC) liquids are derived from common organic compounds by the replacement of all carbon-bound hydrogen atoms with fluorine atoms. These liquids are clear, colorless, odorless, nonflammable, and essentially insoluble in water. PFC liquids are denser than water and soft tissue, and have low surface tension and, for the most part, low viscosity. Perfluorocarbon liquids are unique in their high affinity for gases, dissolving more than 20 times as much $O_2$ and over 3 times as much $CO_2$ as water. Like other highly inert fluorocarbon materials, perfluorocarbon liquids are extremely nontoxic and biocompatible.

In particular, perfluorocarbon liquid ventilation is a promising treatment of respiratory distress syndromes involving surfactant deficiency or dysfunction. Elevated alveolar surface tension plays a central role in the pathophysiology of the Respiratory Distress Syndrome (RDS) of prematurity and is thought to contribute to lung dysfunction in the Adult Respiratory Distress Syndrome. Perfluorocarbon liquid ventilation is effective in surfactant-deficient premature animals because it eliminates air/fluid interfaces in the lung and thereby greatly reduces pulmonary surface tension. Liquid ventilation can be accomplished at acceptable alveolar pressures without impairing cardiac output and provides excellent gas exchange even in very premature animals.

In liquid ventilation, perfluorocarbon liquid is extracorporeally oxygenated and purged of carbon dioxide, and tidal breaths of the liquid are mechanically cycled into and out of the lungs. Many investigators have utilized gravity-induced ventilation whereby reservoirs above and below the level of the patient's lungs induce inspiration and expiration respectively.

As an alternative to such gravity based systems, pumped liquid ventilators have been used. However, these systems have generally been complex in nature, having two or more peristaltic pumps and fluorocarbon reservoirs in order to provide sufficient user control over inspiration, expiration, tube priming, and other functions performed by the ventilation system.

SUMMARY OF THE INVENTION

As liquid ventilation enters widespread use in a clinical, rather than laboratory setting, ventilators which are inexpensive to operate and plumb, which minimize investment in equipment, and which operate with a minimum of extracorporeal fluorocarbon are desirable. Prior art systems sacrifice simplicity for user control, or sacrifice user control for simplicity. The present invention is therefore directed at providing a liquid ventilator which is easy and inexpensive to manufacture, maintain, and use, is efficient, safe, and allows maximum user control over inspiration and expiration parameters.

In one aspect of the present invention, a simplified liquid ventilator which nonetheless allows complete inspiration/expiration control by the operator is provided. Most preferably, the system uses a single pump to force fluorocarbon or other gas dissolving liquid through both a ventilation loop and a regeneration loop. This "dual loop" arrangement produces a liquid ventilation system which is cost effective and simple to plumb, and further is adapted to maximize operator control over inspiration volume, inspiration and expiration flow rates, and priming.

Accordingly, a preferred embodiment of the present invention includes a liquid ventilator comprising a ventilation loop defined by a plurality of interconnected sections of conduit in fluid conducting communication with a regeneration loop defined by a plurality of interconnected sections of conduit. The ventilation loop will be capable of delivering and removing the expired breathable liquid from the pulmonary air passages of a patient while the regeneration loop is capable of treating (i.e. oxygenating) the breathable liquid circulating through the loops. Fluid conducting communication is established by a common section of conduit which comprises a portion of both the ventilation loop and the regeneration loop. Preferably, the section of conduit common to both the ventilation loop and the regeneration loop incorporates a series connected pump for pumping or circulating liquid around both the ventilation loop and the regeneration loop. This reduces cost and simplifies ventilator design because a single pump receives oxygenated liquid for delivery to the patient, and also receives deoxygenated liquid for delivery to a regenerator.

In concordance with this novel and inventive principle, the present invention also comprises a method of ventilating a patient with an oxygenated liquid comprising the steps of placing an endotracheal tube in fluid conducting communication with the pulmonary system of a patient and operably associated with a liquid pump. Oxygenated breathable liquid is then pumped through the endotracheal tube and into the patient's pulmonary air passages where it is subsequently removed by pumping the deoxygenated expired liquid out of the endotracheal tube and out of the patient's pulmonary air passages using the same pump. That is, the pump is used to generate negative pressure on the liquid in the pulmonary air passages essentially suctioning it from the patient.

The utilization of a common pump is improved by controlled routing or directing of liquid through the liquid ventilator system. The routing function is preferably accomplished through the use of valves including, but not limited to, two-way valves and three-way valves. In selected embodiments of the present invention, two valves are preferably used in concert to provide the routing or direction of the breathable liquid. Accordingly, one preferred embodiment of the present invention comprises a liquid ventilator having an endotracheal tube, a pump, a regeneration apparatus for treating the liquid, and two three-way valves for appropriately directing the fluid therebetween. In this embodiment, a first valve is connected to (1) an endotracheal tube via a first conduit, (2) a regeneration apparatus output via a second conduit, and (3) a pump input via a third conduit, whereby either oxygenated liquid from the regeneration apparatus output or carbon dioxide enriched and de-oxygenated expired liquid from the patient may be delivered to the pump input. Furthermore, a second valve is connected to (1) the endotracheal tube via a fourth conduit, (2) the regeneration apparatus input via a fifth conduit, and (3) the pump output via a sixth conduit, whereby either expired liquid may be delivered to the regeneration apparatus input or oxygenated, treated liquid may be delivered to the patient. Of course, it will be appreciated that functionally equivalent ventilation systems comprising two-way valves or combinations of two-way valves and three-way valves are also compatible with the teachings herein.

Because inspiration and expiration normally occur at different flow rates, a liquid ventilator according to one aspect of the present invention includes a controller which may be associated with system components such as valves or the pump. In such embodiments, the liquid ventilation apparatus preferably comprises an inspiration conduit and an expiration conduit, both of which are connected to a pump for pumping liquid to and from a patient. Typically the controller will be operably associated with the system and is preferably capable of controlling the speed and flow rate of the pump. In particularly preferred embodiments the controller is configured to operate the pump at a first speed when pumping liquid to a patient and at a second different speed when pumping expired liquid from a patient. Controllers may also be used to actuate the valves in concert with pump operation so as to provide a coordinated ventilation cycle. Those skilled in the art will appreciate that the controller or controllers may be electronic, fluidic or pneumatic in nature. In any event, regulation of inspiration and expiration parameters will provide for more efficient ventilation of the patient than is possible with prior art multi-pump systems.

Other objects, features and advantages of the present invention will be apparent to those skilled in the art from a consideration of the following detailed description of preferred exemplary embodiments thereof taken in conjunction with the Figures which will first be described briefly.

DETAILED DESCRIPTION OF THE PREFERRED EMBODIMENT

Preferred embodiments of the present invention will now be described with reference to the accompanying Figures, wherein like numerals refer to like elements throughout. The terminology used in the description presented herein is intended to be interpreted in its broadest reasonable manner, even though it is being utilized in conjunction with a detailed description of certain specific preferred embodiments of the present invention. This is further emphasized below with respect to some particular terms. Any terminology intended to be interpreted by the reader in any manner more restrictive than that provided by its ordinary meaning will be overtly and specifically defined as such in this specification.

Figure 1:
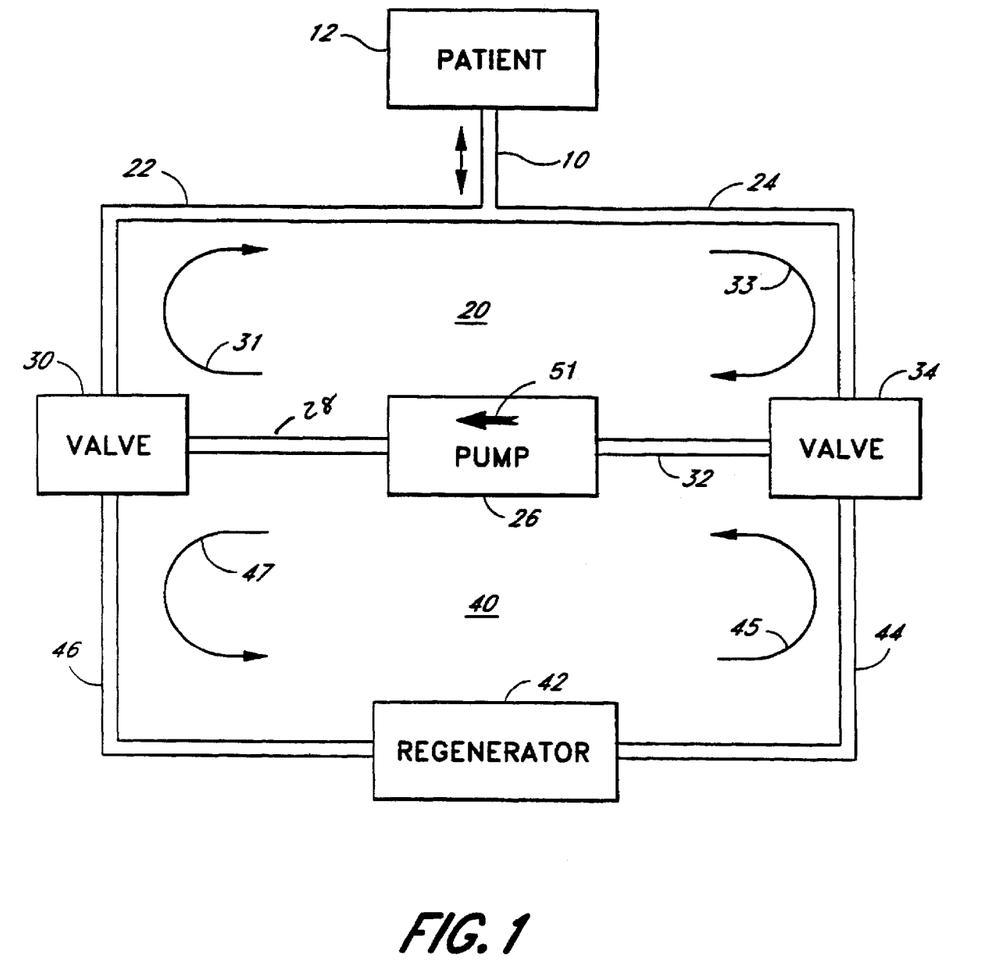
FIG. 1 is a schematic illustration of a preferred embodiment of a dual loop liquid ventilator according to the present invention.

Referring now to FIG. 1, a preferred embodiment of a liquid ventilator incorporating the principles of the present invention is illustrated. The system of FIG. 1 comprises an endotracheal tube 10 which has one end inserted into the trachea of a patient 12 for delivering oxygenated liquid and removing expired liquid from the patient's pulmonary air passages. The endotracheal tube 10 typically comprises a conduit made of polymer tubing of material and configuration well known to those of skill in the art. The breathable liquid is preferably routed throughout the system of the present invention inside conduits of flexible tubing (i.e. polymeric or plastic tubing) which are well known to those of skill in the art, and which are also suitable for gravity feed and multi-pump liquid ventilators. However, the term conduit is intended to include any type of pipe, channel, or other flexible or rigid device creating a passage through which liquid may flow.

As discussed above, the breathable liquid preferably comprises a fluorocarbon, although other gas dissolving liquids may be suitable with the liquid ventilator of the present invention. Specific embodiments of suitable liquid oxygen and carbon dioxide carriers are well known to those of skill in the art, with the bis(F-alkyl) ethanes such as F-44E and F-66E, as well as perfluorodecalin and perfluorooctyl bromide being examples of suitable fluorocarbons for pulmonary oxygen delivery and carbon dioxide removal. Accordingly, for the purposes of the instant application the terms "breathable liquid" and "fluorocarbon" shall be used interchangeably unless indicated otherwise by the contextual placement.

In any event, the other end of the endotracheal tube 10 is connected to a "patient side" ventilation loop, designated generally at 20 in FIG. 1. The ventilation loop 20 is formed from the connection of the non-patient end of the endotracheal tube 10 to an inspiration conduit 22 and an expiration conduit 24. These conduits 22, 24 may advantageously be joined to the non-patient end of the endotracheal tube 10 using a T or Y connector. It is one feature of this preferred embodiment of the present invention that both the inspiration conduit 22 and expiration conduit 24 are served by a common pump 26. As shown in FIG. 1, pump 26 is connected through a pump output conduit 28 to a pump output valve 30. Preferably pump output valve 30 is a three-way valve although other valve configurations such as two-way valves may be adapted for use in the present invention. As will be explained more fully below, pump output valve 30 may be set to route pump output conduit 28 to inspiration conduit 22 in order to allow pump 26 to force oxygenated fluorocarbon through inspiration conduit 22 and endotracheal tube 10 and into the patient's pulmonary air passages, generally in the direction of arrow 31 of FIG. 1. Similarly, pump 26 is connected through a pump input conduit 32 to pump input valve 34. Again, pump input valve 34 is preferably a three-way valve although other valve configurations such as two-way valves are contemplated as being within the scope of the invention. As will also be explained more fully below, pump input valve 34 may be set to route the expiration conduit 24 to the pump input conduit 32 in order to allow pump 26 to pull carbon dioxide enriched and deoxygenated expired liquid fluorocarbon out of the patient's pulmonary air passages through the endotracheal tube 10 and expiration conduit 24, toward pump 26, generally in the direction of arrow 33.

In the preferred ventilator embodiment of FIG. 1, pump 26, pump input conduit 32 and pump output conduit 28 further comprise one portion of a regeneration loop, designated generally as 40 in FIG. 1. Regeneration loop 40 comprises a regenerator 42 for treating the circulating liquid, primarily by removing carbon dioxide and oxygenating the fluorocarbon, i.e. it may be used to adjust the levels of dissolved oxygen or dissolved carbon dioxide present in the breathable liquid. In preferred embodiments, regenerator 42 may also be used to further treat the liquid by adjusting the temperature of the fluorocarbon. Additionally, regenerator 42 may comprise a means to condense or otherwise conserve fluorocarbon vapor (a liquid conservation device) generated during the therapeutic procedure. The regenerator is connected to an output conduit 44 for routing heated and oxygenated fluorocarbon to the pump input valve 34, generally in the direction of arrow 45. The regenerator is further connected to an input conduit 46 connecting the regenerator to the pump output valve 30, so that the regenerator may receive, from the general direction of arrow 47, carbon dioxide-enriched and de-oxygenated expired fluorocarbon for regeneration. In preferred embodiments regenerator 42 further comprises a reservoir of breathable liquid (i.e. a fluorocarbon) that may be oxygenated or deoxygenated.

The inspiration and expiration phases of a ventilation cycle of this preferred embodiment of the present invention can now be understood. During an inspiration phase, the pump input valve is preferably set to connect the regenerator output conduit 44 to the pump input conduit, and to block flow to and from the expiration conduit 24 at the valve 34. Pumping action of pump 26 in the direction of arrow 51 therefore pulls oxygenated fluorocarbon from the reservoir in the regenerator 42, and toward the pump output valve 30, which is set to route fluorocarbon flow from the pump output conduit 28 to the inspiration conduit 22, and to block flow to and from the regenerator input conduit 46. Additional components or decontaminating devices may be associated with the apparatus (preferably with expiration conduit 28 and inspiration conduit 22) for removal of gas bubbles, particulates, biological material or aqueous material from the breathable liquid. As the expiration conduit 24 is also blocked at the pump input valve 34, the oxygenated fluorocarbon is therefore forced into the endotracheal tube 10 and into the patient. During inspiration, therefore, the oxygenated fluorocarbon travels from the regenerator in the direction of arrows 45 and 31 to the patient 12.

During an expiration phase, pump input valve 34 is set to connect the expiration conduit 24 to the pump input conduit 32, and to block flow to and from the regenerator output conduit 44 at valve 34. Pumping action of pump 26 in the direction of arrow 51 therefore pulls carbon dioxide enriched and de-oxygenated fluorocarbon from patient 12, and toward the pump output valve 30, which is set to route fluorocarbon flow from the pump output conduit 28 to the regenerator input conduit 46, and to block flow to and from the inspiration conduit 22. During expiration, therefore, the carbon dioxide enriched and de-oxygenated fluorocarbon travels from the patient in the direction of arrows 33 and 47 to the regenerator 42.

One aspect of the present invention is therefore a dual loop liquid ventilator. Preferably, one of the loops 20 is a ventilation loop comprising an endotracheal tube 10 for patient delivery of oxygenated liquid, and the second separate loop is a regeneration loop 40 comprising oxygenation apparatus. Most preferably, both loops additionally comprise a common conduit which includes a single series connected pump 26, wherein flow through the regeneration loop 40 and flow through the ventilation loop 20 are both mediated by the single, common pump 26. Of course the ventilation systems of the present invention may comprise additional elements such as filters for removing impurities in the circulating liquid or conservation devices for reducing or eliminating the loss of liquid vapor during the procedure. Of course such devices may be operably associated with the ventilation apparatus at any appropriate point and in any compatible configuration.

It can be appreciated that although a preferred dual loop ventilation system has been described above in terms of six different conduit sections, namely, pump 26, input and output conduits 32, 28, inspiration and expiration conduits 22, 24, and regeneration input and output conduits 46, 44, some of these separate sections may be comprised of a single physical conduit. For example, when pump 26 is a roller type peristaltic pump, the pump input and output conduits 32, 28 may actually comprise a continuous piece of flexible plastic tubing. In such embodiments, one section of the common conduit comprises a pump input and pump output portion. The same holds true for other sections of conduit in the above described system, as the definition of a conduit section is determined by how the section is connected to other portions of the system, rather than by any physical boundaries between sections which may or may not be present.

Figure 2:
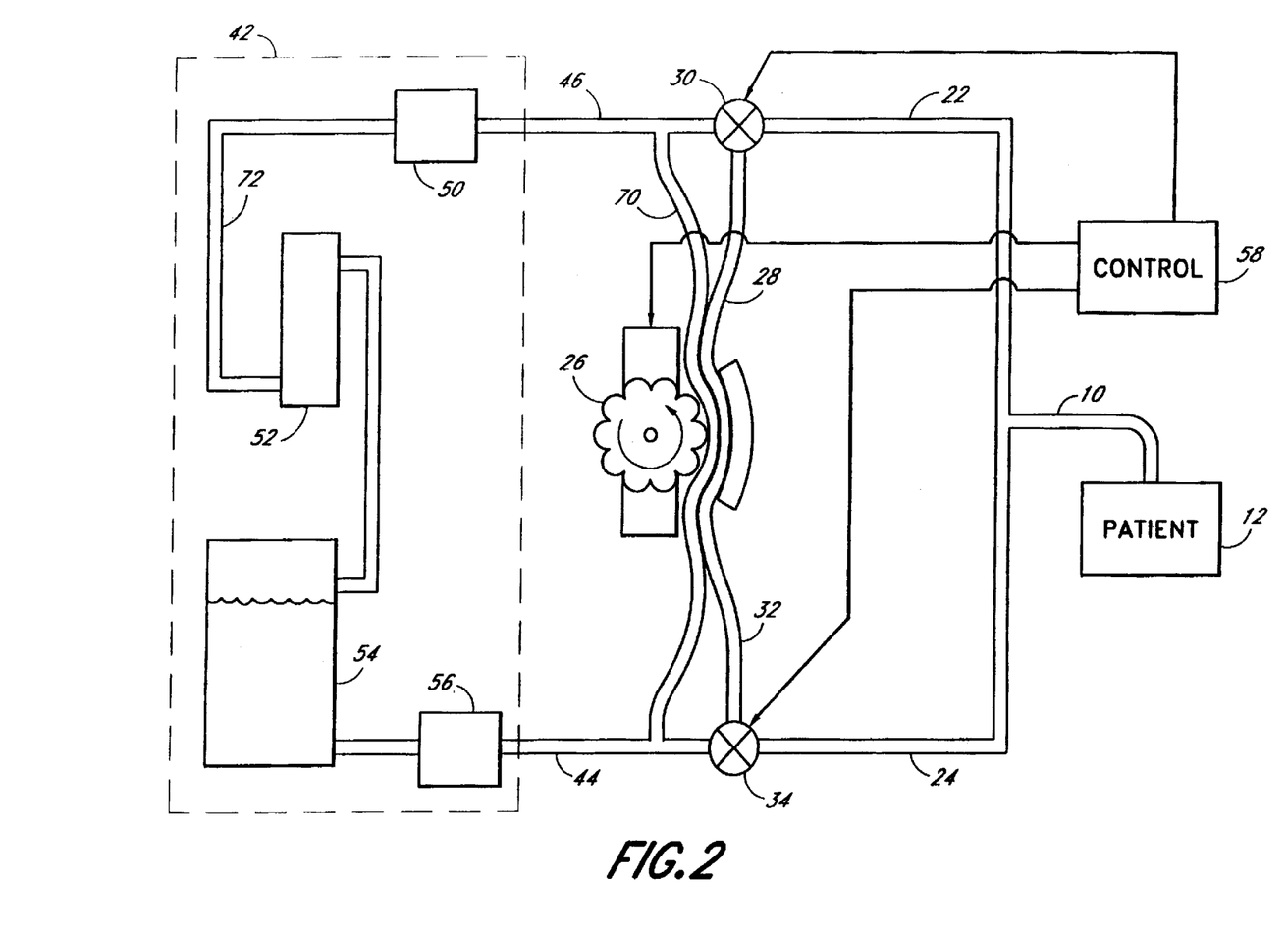
FIG. 2 is a schematic illustration of a preferred embodiment of a dual loop liquid ventilator according to the present invention.

Having thus described the general principles of a preferred embodiment of the present invention, a more detailed illustration of such a system is presented in FIGS. 2 through 7. Referring now to these Figures, it can be appreciated that the regenerator 42 typically comprises several separate components. For example, as illustrated in FIG. 2, the regenerator input conduit 46 may be fed to a bubble trap/filter 50 to filter out bubbles and particulate material which is often present in exhaled liquid fluorocarbon from patient 12. The fluorocarbon is then passed to a gas exchanger 52 for $CO_2$ removal and oxygenation. This unit may, for example, be of a membrane or bubble type, each configuration being well known to those in the art. Oxygenated fluorocarbon is then routed to a reservoir 54. The volume of reservoir 54 may vary depending on the lung capacity of the patient, i.e. whether an adult or infant is to be ventilated. It is preferable to minimize the excess capacity of the reservoir 54, so as to minimize the amount of fluorocarbon required to prime and operate the system. It will be appreciated that reservoir 54 may be open to ambient pressure or sealed, at least partially, to conserve fluorocarbon vapor which otherwise may escape.

At the output of the reservoir 54 is an optional heat exchanger 56 for ensuring that the fluorocarbon being delivered to the patient 12 is at an appropriate temperature. As with other individual components of the regeneration apparatus 42, the heat exchanger 56 can take many forms well known to those in the art, and will not be described in more detail herein.

In selected embodiments pump 26 may be a roller type peristaltic pump although other pump types are suitable for use with the present ventilator system and are clearly within the purview of the instant invention. Pump speed, flow rate, etc., is preferably controlled by a host controller 58 which may operate through electronic, fluidic or pneumatic principles. That is, controller 58 may be used to alter the operating speed of the pump during the ventilation procedure. In this respect, it is often desirable to have differing inspiration and expiration flow rates. Typically, the expiration cycle is longer than the inspiration cycle, although the volume of liquid transferred will be equal. It is therefore preferable to run the pump 26 at a slower rate during expiration than during inspiration. This rate change is preferably programmed into the controller 58. Valves 30, 34 (i.e. three-way valves) are also preferably actuated in response to signals from controller 58 whereby the direction of liquid flow through valves 30, 34 may be determined. Of course, separate controllers may be used for the actuation of the valves and determination of pump speed. In any case, it is preferable that pump speed be appropriately timed to the positions of valves 30, 34 to coordinate flow rates with the inspiration and expiration phases of the ventilation cycle.

Figure 3A:
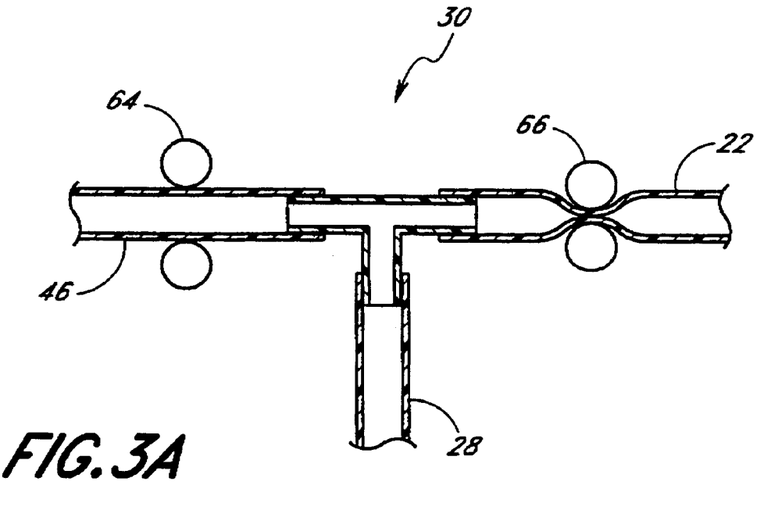
FIGS. 3A–3B are cutaway views of one preferred embodiment of the three-way valves of FIG. 2 during an expiration phase.
Figure 3B:
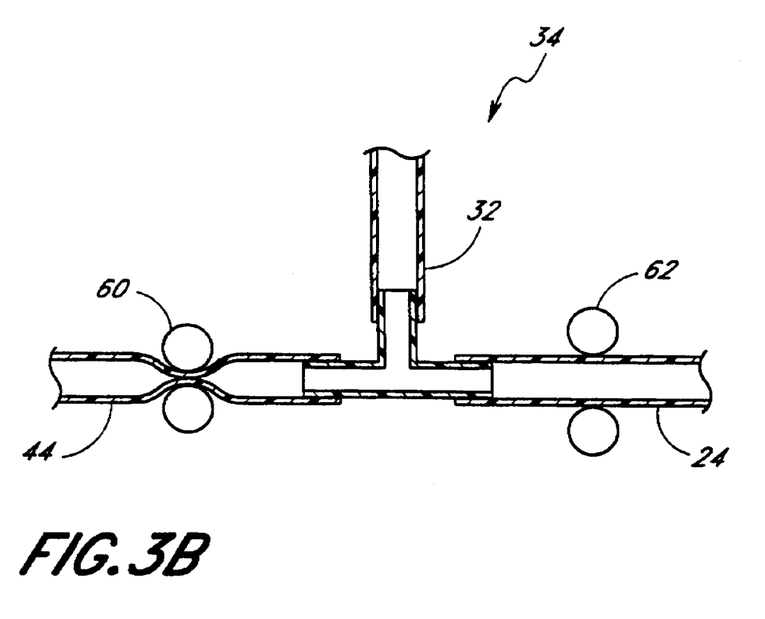

Referring now to FIGS. 3A–3B, valves 30, 34 may each comprise a T-connector and two tubing pinch type one-way valves although other compatible valve assemblies are also contemplated. FIG. 3B illustrates the valve actuation configuration for an expiration phase of the ventilation cycle. As shown in FIG. 3B, the pump input valve 34 is formed by situating a first tubing pinch type valve 60 in the regenerator output conduit 44 and a second tubing pinch type valve 62 in the expiration conduit 24, both preferably near the connection point to the pump input conduit 32. Analogously, the pump output valve 30 is formed by situating a third tubing pinch type valve 64 in the regenerator input conduit 46 and a fourth tubing pinch type valve 66 in the inspiration conduit 22, wherein again both are preferably near the connection point to the pump output conduit 32. During the expiration phase, the pinch valve 60 in the regeneration output conduit 44 and the pinch valve 66 in the inspiration conduit 22 are actuated to cut off flow from the regenerator 42 and to the endotracheal tube 10. Alternatively, during an inspiration phase, the other two pinch valves 62, 64 are actuated. As will be explained more fully below with reference to FIGS. 6 through 8, tube sweeping and priming phases can also be run using appropriate choices of pinch valve actuation.

The tubing pinch valve embodiment described above has an advantage in that the valves themselves are not in contact with the fluorocarbon. When the apparatus is to be used on a different patient, therefore, only the tubing needs to be replaced, and the valves themselves are re-used. This simplifies sterilization, as valves need not be sterilized or thrown away with each use. Those of skill in the art will still appreciate, however, that many different types of valves are devisable and commercially available for use as pump input and pump output valves 30, 34, with the tubing pinch type described above being merely one example. Solenoid actuated or rotating two-way or three-way valves may be utilized, with cost and quality being especially relevant to a determination of what valve type is most suitable. Most preferably, however, and in accordance with the above description of ventilator operation, valves 30, 34 should each comprise mechanisms which allow flow from a first input/output conduit to second and/or third input/output conduits, wherein the flow connections can be made either independently (as in the pinch valve embodiment discussed above with reference to FIG. 3) or in an alternative fashion (as in some commercially available electromechanical valves).

In this regard, one example of a commercially available tubing pinch type valve suitable for use in an embodiment of the present invention is the E-01367-94 from Cole-Parmer of Vernon Hills, Ill. An example of a commercially available electromechanical valve suitable for use in an embodiment of the present invention is the E-98300-32 from Cole-Parmer.

As is further illustrated by the embodiment of FIG. 3 wherein the valves comprise two one way valves, the flow regulating mechanisms of valves 30, 34 (here three-way valves) need not be part of a single, integral apparatus, but may be located at separate locations of the liquid ventilator system. Valves 30, 34, are preferably also controlled by controller 58, thereby coordinating the flow paths at the valves 30, 34 with pump 26 speed to produce the desired rate and volume of inspiration and expiration cycles.

With such a ventilation system, gas exchange is more efficient than prior art designs. Because only exhaled fluid is routed to the regeneration apparatus, a relatively high $CO_2$ gradient is present in the gas exchanger. This will increase exchange efficiency. Also, because fluid through in the regeneration loop stops during inspiration, extra dwell time inside the gas exchanger is created, further improving gas exchange.

As an alternative, gas exchange may be improved by running fluid through the regeneration loop more than once for every time the fluid passes through the ventilation loop. Referring back now to FIG. 2, this feature may be incorporated by providing a second regeneration path with a second pumped conduit 70 which also runs through the peristaltic pump 26, but which bypasses valves 30, 34. Instead, the second pumped conduit 70 is directly connected to the regenerator output conduit 44 at one end, and to the regenerator input conduit 46 on the other end, so that pump 26 action continuously pumps fluorocarbon in the reservoir 54 back through the regeneration apparatus. This extra regeneration loop can improve gas exchange by increasing the flow through the gas exchanger 52 as set forth immediately below.

During inspiration, flow through the gas exchanger 52 will be equal to the inspiration flow rate. During expiration, flow through the gas exchanger will be approximately double the expiration flow rate. The total amount of fluorocarbon passing through the gas exchanger per minute will therefore be approximately three times the amount of fluorocarbon being processed by the pulmonary system of the patient 12. It may also be noted that if the expiration flow rate is half that of the inspiration flow rate, the flow rate of fluorocarbon through the gas exchanger 52 will be nearly constant. In some instances, it may also be desirable to bypass the filter/bubble trap 50, and connect one end of the second pumped conduit 70 directly to the input side 72 of the gas exchanger 52, rather than to the regenerator input conduit 46.

Figure 4:
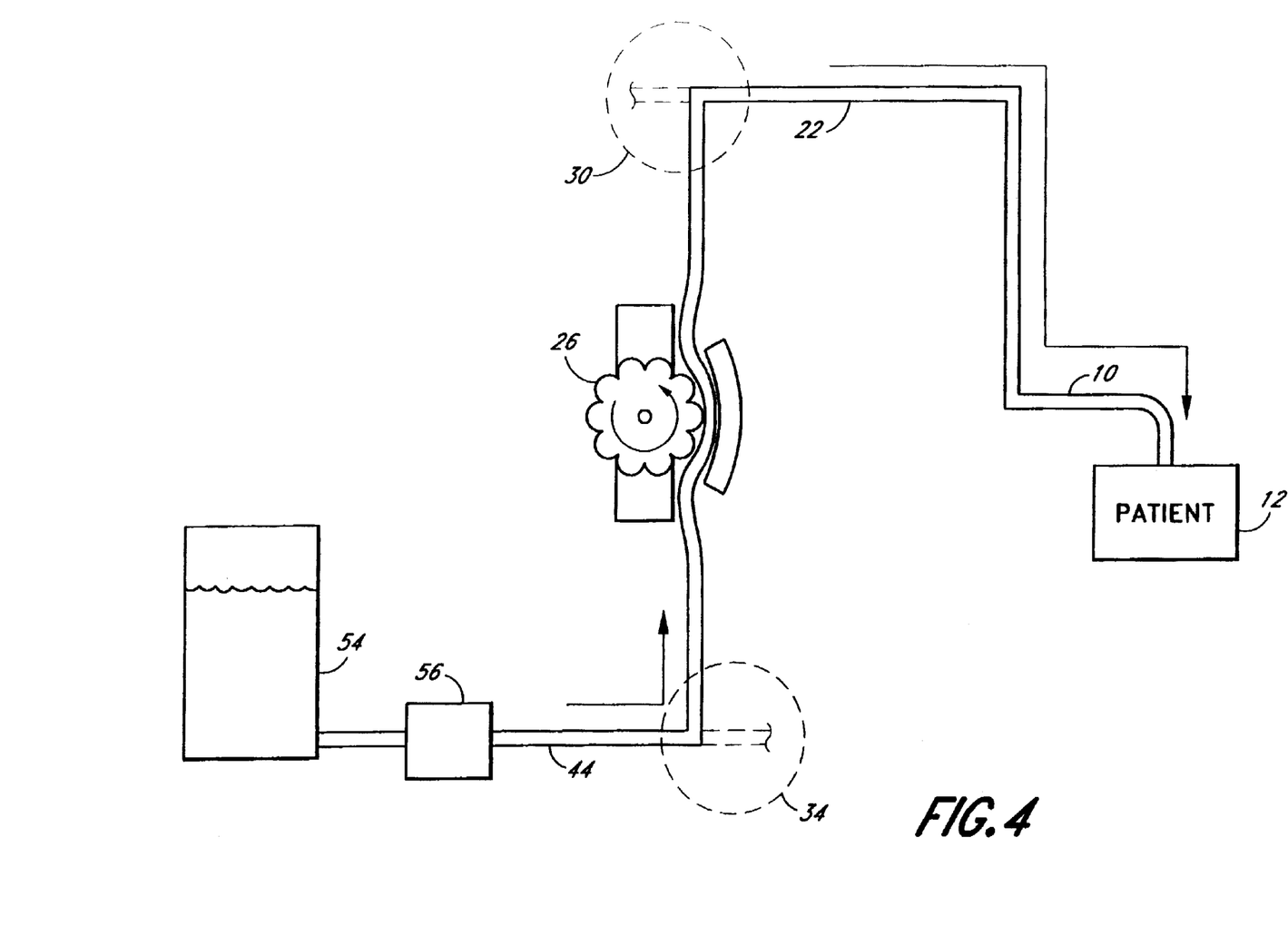
FIG. 4 is a partial schematic of a preferred liquid ventilator according to the present invention illustrating an inspiration phase.
Figure 5:
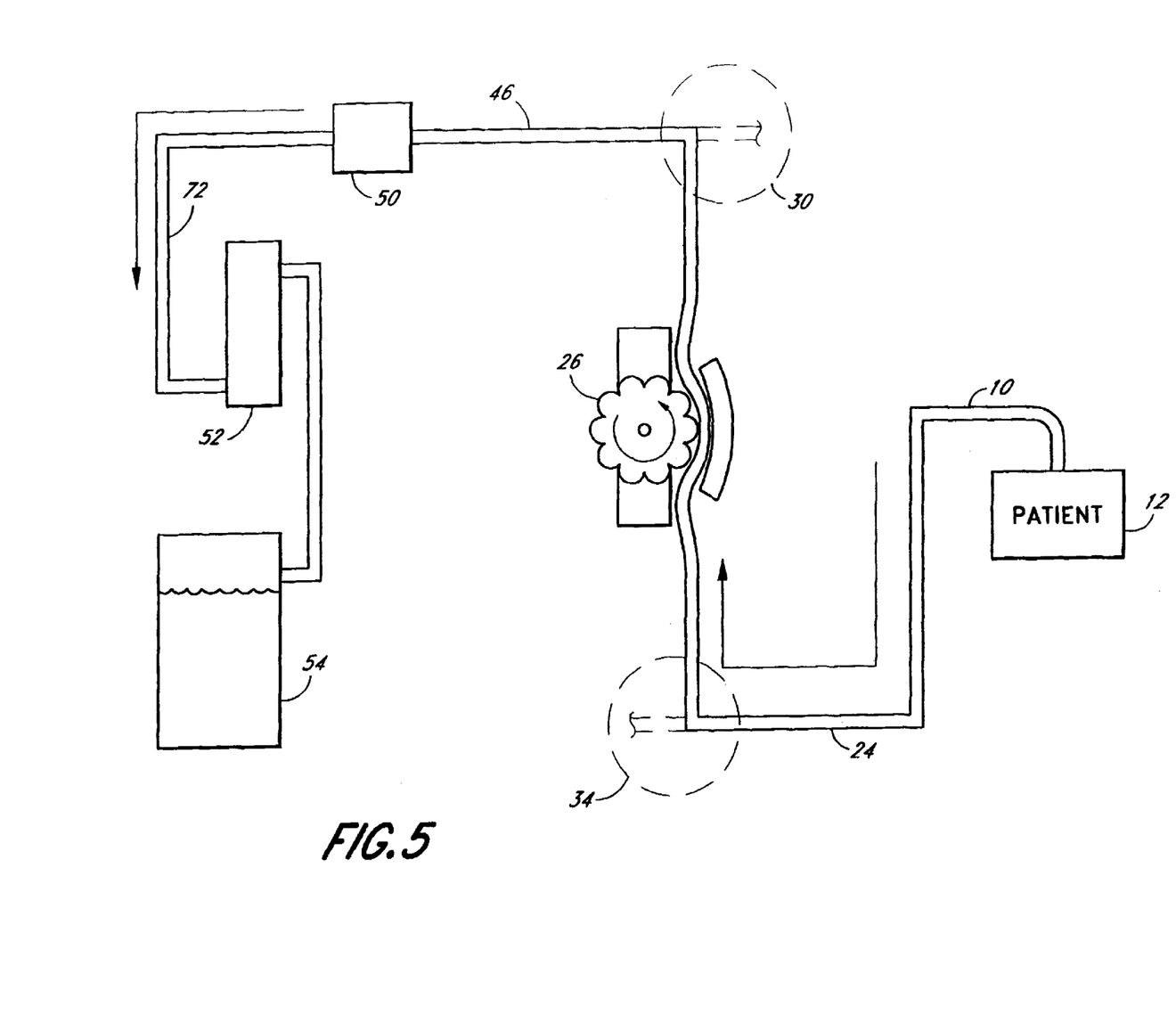
FIG. 5 is a partial schematic of a preferred liquid ventilator according to the present invention illustrating an expiration phase.

FIGS. 4 and 5 illustrate the effect of valve 30, 34 configurations which produce an inspiration phase (shown in FIG. 4) and an expiration phase (shown in FIG. 5). As can be seen by examination of FIG. 4, during inspiration, fluorocarbon flows out of the reservoir 54, through the pump 26, and into the endotracheal tube 10 to the patient 12. During expiration, the fluorocarbon flows out of the patient 12, through the pump 26, and into the gas exchanger 52 to the reservoir 54. Therefore, although fluorocarbon flows through alternate portions of the ventilation loop and regeneration loop during inspiration and expiration, the direction of flow through the pump 26 remains the same.

Figure 6:
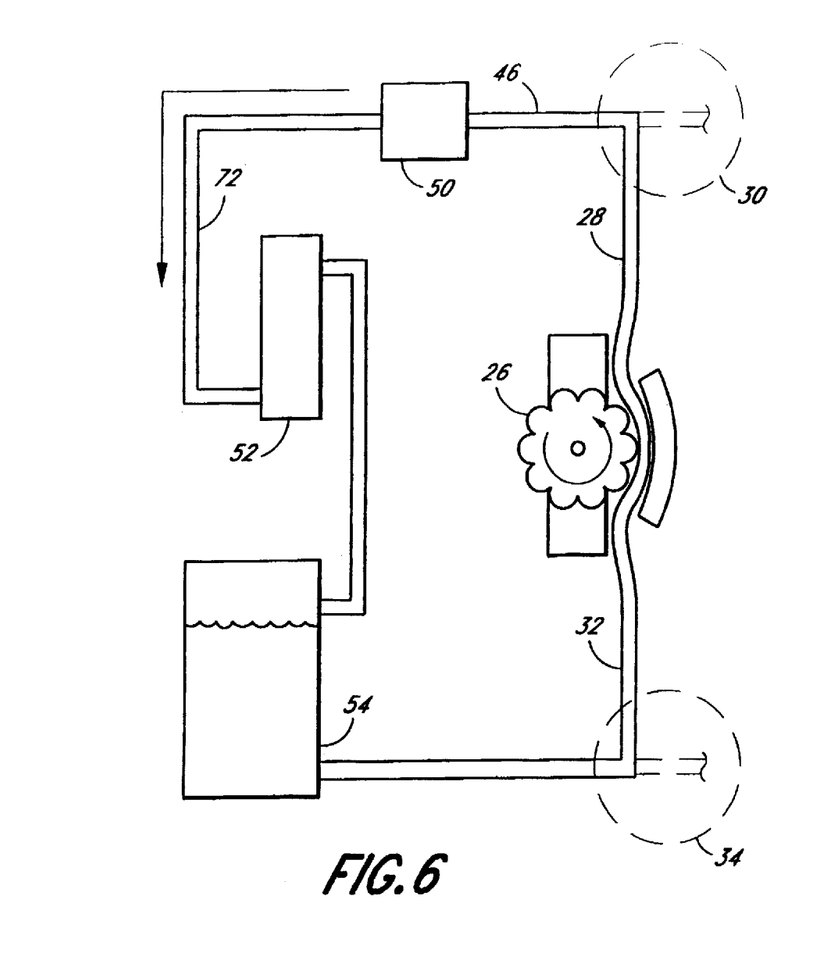
FIG. 6 is a partial schematic of a preferred liquid ventilator according to the present invention illustrating a sweeping phase.

FIG. 6 illustrates the effect of configuring valves 30, 34 such that flow to and from both the inspiration conduit 22 and expiration conduit 24 are blocked off from the pump output conduit 28 and pump input conduit 32 respectively.

In this configuration, fluorocarbon in the pump input and output conduits 28, 32 is routed to the regenerator apparatus 42, and is replaced by oxygenated fluorocarbon from the reservoir 54. This may therefore be termed a "sweep" operation, and is preferably performed between the expiration and inspiration phases of the ventilation cycle to sweep the pump input and output conduits 28, 32 of carbon dioxide enriched and de-oxygenated fluorocarbon from the preceding expiration.

Figure 7:
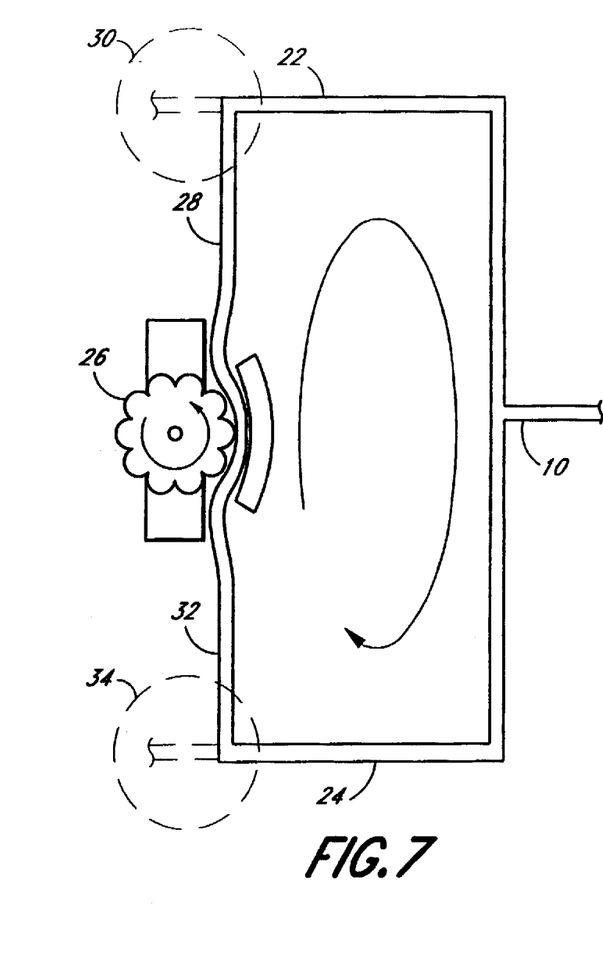
FIG. 7 is a partial schematic of a preferred liquid ventilator according to the present invention illustrating the priming phase.

FIG. 7 illustrates a ventilation loop priming operation. In this instance, valves 30, 34 are configured to prevent flow into and out of the regenerator input conduit 46 and regenerator output conduit 44. Fluorocarbon flow is therefore solely through the ventilation loop 20. Of course, endotracheal tube 10 is capped during this priming operation. At the start of the priming phase, the pump input conduit 32 and pump output conduit 28 should be filled with oxygenated fluorocarbon from the reservoir 54, while the rest of the ventilation loop 20 may be either empty or filled with carbon dioxide enriched and de-oxygenated fluorocarbon. During the priming phase, the oxygenated fluorocarbon is moved from the pump input and output conduits 32, 28 and into the inspiration and expiration conduits 22, 24. Most preferably, the sweeping phase and priming phase are alternated.

In this manner, the pump input and output conduits 32, 28 are first filled with oxygenated fluorocarbon during a sweeping phase as shown in FIG. 6. The three way valves are then switched to the priming configuration as shown in FIG. 7, and remain there until the oxygenated fluorocarbon from the pump input and output conduits 32, 28 is pumped into the inspiration conduit 22. The three-way valves are then switched back to the sweeping configuration to refill the pump input and output conduits 32, 28 with oxygenated fluorocarbon, which is then pumped to the inspiration conduit 22 in a repeat of the priming phase previously performed. This alternation between sweeping and priming is continued until the inspiration conduit 22 and expiration conduit 24 are primed with freshly oxygenated fluorocarbon from the reservoir 54.

Figure 8:
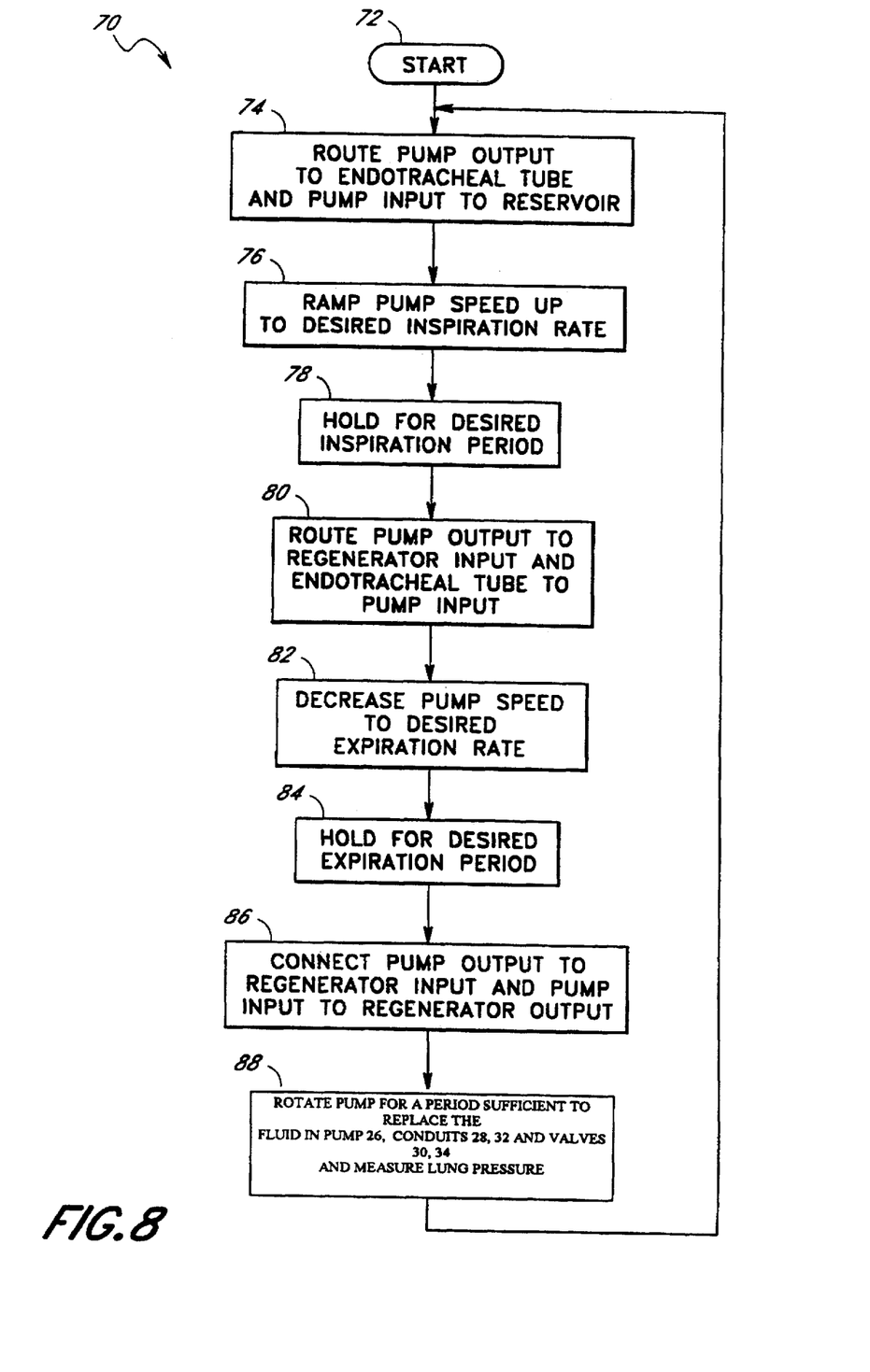
FIG. 8 is a flowchart of an inspiration/expiration/sweeping cycle utilizing a preferred embodiment of a liquid ventilator according to the present invention.

Having now described the various modes of fluorocarbon flow which are preferably effected by a dual loop, single pump embodiment of the present invention, a flowchart of a preferable complete ventilation cycle is presented in FIG. 8. The steps recited herein are preferably programmed into the controller 58 which directs (preferably electrically) the configuration of valves 30, 34 and pump 26 speed in accordance with user defined parameters to properly time the valve configurations and pump speeds which produce the ventilation cycle herein described.

Following several alternating sweep and prime phases as described above with reference to FIGS. 6 and 7, and with the patient's 12 pulmonary system flushed with fluorocarbon, the ventilation cycle 71 begins at START block 73 of FIG. 8. An inspiration phase is begun at step 74 by routing flow from the pump output conduit 28 only to the inspiration conduit 22 via the pump output valve 30. At the same time, the pump input valve 34 is configured to route only the regenerator output conduit 44 to the pump input conduit 32. When the valves 30, 34 are thus set for this inspiration phase, the pump, as will be explained in more detail below, is running at the slower expiration phase rate. Accordingly, at step 76, the pump speed is ramped up to the desired inspiration flow rate. Starting the inspiration phase flow rate at the slower expiration phase flow rate helps minimize any transient pressure build up behind valves 30, 34 immediately prior to switching them to the inspiration configuration. At step 78, the inspiration fluorocarbon flow is continued until the desired tidal volume has been delivered to the patient 12.

At step 80, an expiration phase is then begun by resetting the pump output valve 30 to route fluorocarbon flow from the pump output conduit only to the regenerator input conduit 46. At the same time, the pump input valve 34 is reset to allow fluorocarbon flow to the pump input conduit 32 to occur only from the expiration conduit 24. This allows expiration from the endotracheal tube 10 to the regenerator 42. Upon the start of the expiration phase, the pump speed is decreased at step 82 to the desired expiration rate. Alternatively, the pump speed may be decreased to the desired expiration rate at the very end of the inspiration cycle, immediately prior to resetting valves 30, 34 for expiration. Expiration flow from the patient 12 is continued until the desired tidal volume has been removed from the patient 12 at step 84.

Because the pump input conduit 32 and the pump output conduit 28 are filled with carbon dioxide enriched and de-oxygenated fluorocarbon immediately following the expiration phase, it is preferable to include a brief sweeping phase prior to initiating the next succeeding inspiration phase. This ensures that no carbon dioxide enriched and de-oxygenated fluorocarbon from the last expiration is reintroduced into the patient during the next inspiration. Accordingly, at step 86 of FIG. 8, the pump output valve 30 is set to only allow flow from the pump output conduit 28 to the regenerator input conduit 46. At the same time, the pump input valve 34 is configured to only allow flow from the regenerator output conduit 44 to the pump input conduit 32. At step 88, the pump 26 continues to pump at the expiration rate for a short period, preferably for a time sufficient to replace the fluid in pump 26, conduits 28, 32 and valves 30, 34 (approximately one or two revolutions for a roller type peristaltic pump), thereby sweeping the common conduit system of carbon dioxide enriched and de-oxygenated fluorocarbon from the last expiration, and replacing it with oxygenated fluorocarbon from the reservoir 54. During this period, when flow in the ventilation loop is stopped, it is preferable to make a measurement of the pressure in the patient side of the endotracheal tube to monitor the alveolar pressure of the patient 12. This measurement is difficult to make accurately during inspiration or expiration, because of the flow induced pressure drop between the endotracheal tube 10 and the lungs themselves.

After this brief sweeping phase, the ventilation cycle 70 loops back to step 74, and configures valves 30, 34 for another inspiration phase as described above. Accordingly, a single pump is effective to service both a regeneration loop and a ventilation loop during each ventilation cycle, thereby providing maximum user control over ventilation parameters, while minimizing ventilator cost and complexity.

The foregoing description details certain preferred embodiments of the present invention and describes the best mode contemplated. It will be appreciated, however, that no matter how detailed the foregoing appears in text, the invention can be practiced in many ways. As is also stated above, it should be noted that the use of particular terminology when describing certain features or aspects of the present invention should not be taken to imply that the ordinary meaning of such terminology is not intended, or that the terminology is being re-defined herein to be restricted to including any specific characteristics of the features or aspects of the invention with which that terminology is associated. The scope of the present invention should therefore be construed in accordance with the appended claims and any equivalents thereof.

What is claimed is:

1. An apparatus for ventilating a patient with oxygenated liquid comprising:
   an endotracheal tube for delivering oxygenated breathable liquid to the patient and for conveying expired liquid from the patient;
   a regeneration apparatus having an input and an output for treating expired breathable liquid;
   a pump having an input and an output; and,
   first and second valves interconnected with said endotracheal tube, said regeneration apparatus, and said pump;
   wherein said first valve is connected to (1) said endotracheal tube via a first conduit, (2) said regeneration apparatus output via a second conduit, and (3) said pump input via a third conduit, whereby either treated breathable liquid from said regeneration apparatus output or expired breathable liquid from the patient may be delivered to said pump input;
   and wherein said second valve is connected to (1) said endotracheal tube via a fourth conduit, (2) said regeneration apparatus input via a fifth conduit, and (3) said pump output via a sixth conduit, whereby either expired breathable liquid may be delivered to said regeneration apparatus input or oxygenated breathable liquid may be delivered to the patient.

2. The apparatus of claim 1 wherein said breathable liquid comprises a fluorocarbon.

3. The apparatus of claim 1 further comprising a controller whereby the operating speed of the pump may be altered.

4. The apparatus of claim 3 wherein said controller may further be used to determine the direction of breathable liquid flow through said first and said second valves.

5. The apparatus of claim 3 or 4 wherein said controller is electrical, fluidic or pneumatic.

6. The apparatus of claim 4 wherein said controller is configured to direct fluid flow in said first valve from said regeneration apparatus output and to said pump input, and wherein said controller is also configured to direct fluid flow in said second valve from said pump output and to said endotracheal tube.

7. The apparatus of claim 4 wherein said controller is configured to direct fluid flow in said first valve from said endotracheal tube and to said pump input, and wherein said controller is also configured to direct fluid flow in said second valve from said pump output and to said regeneration apparatus input.

8. The apparatus of claim 1 wherein said regeneration apparatus is capable of treating the breathable liquid by adjusting the dissolved oxygen content, adjusting the dissolved carbon dioxide content or adjusting the temperature.

9. The apparatus of claim 1 further comprising a liquid conservation device.

10. The apparatus of claim 1 further comprising a decontaminating device for removing contaminants from breathable liquid.

11. A liquid ventilation apparatus, comprising:
    a ventilation loop defined by a plurality of interconnected sections of conduit, said ventilation loop and said regeneration loop comprising a common section of conduit whereby fluid conducting communication is established between the ventilation loop and the regeneration loop; and
    a breathable liquid circulating through the ventilation loop and the regeneration loop wherein the ventilation loop is capable of delivering breathable liquid to a patient and conveying expired breathable liquid from the patient and the regeneration loop is capable of oxygenating the circulating breathable liquid, wherein said common section of conduit is operably associated with a pump in series, said pump capable of circulating said liquid through both the ventilation loop and the regeneration loop.

12. The liquid ventilation apparatus of claim 11 wherein said common section of conduit comprises a first end and a second end, said first and second conduit end associated with a first valve and second valve respectively whereby fluid conducting communication between the regeneration loop and the ventilation loop is established.

13. The liquid ventilation apparatus of claim 12 wherein said first valve and said second valve are three way valves.

14. The liquid ventilation apparatus of claim 12 further comprising a controller whereby the operating speed of the pump may be altered.

15. The liquid ventilation apparatus of claim 14 wherein said controller may further be used to determine the direction of liquid flow through said first and said second valves.

16. The liquid ventilation apparatus of claim 14 or 15 wherein said controller is electrical, fluidic or pneumatic.

17. The liquid ventilation apparatus of claim 11 wherein said regeneration loop is further capable of treating the breathable liquid by adjusting the dissolved carbon dioxide content or adjusting the temperature.

18. The liquid ventilation apparatus of claim 11 further comprising a liquid conservation device.

19. The liquid ventilation apparatus of claim 11 further comprising a decontaminating device for removing contaminants from the circulating breathable liquid.

20. The liquid ventilation apparatus of claim 11 wherein said breathable liquid is a fluorocarbon.

21. The liquid ventilation apparatus of claim 20 wherein said fluorocarbon is selected from the group consisting of perfluorooctyl bromide and perfluorodecalin.

22. A liquid ventilator comprising:
    a pump having an input and an output;
    an endotracheal tube;
    a regenerator having an input and an output;
    first means for alternatively directing liquid from said pump output to said regenerator input or to said endotracheal tube; and,
    second means for alternatively directing liquid from either said regenerator output or said endotracheal tube to said pump input.

23. The liquid ventilator of claim 22 wherein said pump comprises a peristaltic pump.

24. The liquid ventilator of claim 22 wherein said first directing means or said second directing means comprises a valve selected from the group consisting of two-way valves and three-way valves.

25. A method of ventilating a patient with breathable liquid, comprising the steps of:
    providing a reservoir of breathable liquid;
    pumping said breathable liquid from said reservoir with a pump to create a flow of liquid through a first conduit;
    oxygenating the flowing breathable liquid using a regenerator associated with said first conduit to provide a flow of oxygenated breathable liquid;
    directing the flow of oxygenated liquid into the patient's pulmonary air passages wherein the liquid becomes at least partially deoxygenated;
    pumping the deoxygenated liquid from the pulmonary air passages with said pump to create a flow of deoxygenated liquid through a second conduit;
    directing the flow of deoxygenated liquid from said second conduit into said reservoir; and
    sweeping a portion of said first and second conduits of deoxygenated liquid.

* * * * *